US006326505B1

(12) United States Patent
Vaartstra

(10) Patent No.: US 6,326,505 B1
(45) Date of Patent: Dec. 4, 2001

(54) METHODS, COMPLEXES, AND SYSTEM FOR FORMING METAL-CONTAINING FILMS

(75) Inventor: Brian A. Vaartstra, Nampa, ID (US)

(73) Assignee: Micron Technology, Inc., Boise, ID (US)

( * ) Notice: Subject to any disclaimer, the term of this patent is extended or adjusted under 35 U.S.C. 154(b) by 0 days.

(21) Appl. No.: 09/309,825

(22) Filed: May 11, 1999

Related U.S. Application Data

(62) Division of application No. 08/725,064, filed on Oct. 2, 1996, now Pat. No. 5,924,012.

(51) Int. Cl.⁷ .................................. C07F 5/06; C07F 5/00
(52) U.S. Cl. ............................. 556/1; 556/175; 556/176; 427/248.1; 438/681; 118/715
(58) Field of Search ................................ 556/1, 175, 176; 438/681; 427/248.1

(56) References Cited

U.S. PATENT DOCUMENTS

| | | | |
|---|---|---|---|
| 5,015,747 | 5/1991 | Hostalek et al. | 556/1 |
| 5,036,022 | 7/1991 | Kuech et al. | 437/81 |
| 5,084,128 | 1/1992 | Baker | 156/614 |
| 5,112,432 | 5/1992 | Erdmann et al. | 156/610 |
| 5,180,687 | 1/1993 | Mikoshiba et al. | 437/187 |
| 5,259,915 | 11/1993 | Pohl et al. | 156/600 |
| 5,451,260 | 9/1995 | Versteeg et al. | 118/725 |
| 5,545,591 | 8/1996 | Sugai et al. | 437/192 |
| 5,607,722 | 3/1997 | Vaartsrta et al. | 427/248.1 |
| 5,659,057 | 8/1997 | Vaartstra | 556/51 |
| 5,863,836 | 1/1999 | Jones | 438/681 |
| 5,924,012 | 7/1999 | Vaartstra | 438/681 |

FOREIGN PATENT DOCUMENTS

| | | |
|---|---|---|
| 295 876 | 11/1991 | (DD) . |
| 42 13 292 A1 | 10/1993 | (DE) . |
| 4213292 | 10/1993 | (DE) . |

OTHER PUBLICATIONS

Hostalek et al., "Novel Organometallic Starting Materials for Group III–V Semiconductor Metal–Organic Chemical Vapour Deposition," *Thin Solid Films* 174: 1–4 (1989).

Leung et al., "Synthesis and structural characterisation of mono– and bi– nuclear cobalt(II) alkyls," *J. Chem. Soc. Dalton Trans*. 779–783 (1997).

Scherer et al., "Amine–Stabilized Cyclopentadienyl Diisobutyl Aluminum Complexes as New Kinds of Precursors for the Deposition of thin Aluminum Films by CVD," *Chem. Vap. Deposition* 3:33–35 (1997).

Schumann et al., "Intramolecularly Stabilized Organoaluminum –gallium and –indium Derivatives/Crystal Structures of {o–[(Diethylamino) methyl]phenyl} dimethygallium and {o–[(Dimethylamino ) methly]Phenyl}dimethylindium," *Chem. Ber.* 123:2093–2099 (1990).

Singer, "Filling Contacts and Vias: A Progress Report," *Semiconductor Int'l* 89–90, 92, 94 (1996).

Versteeg et al., "Metalorganic Chemical Vapor Deposition By Pulsed Liquid Injection Using An Ultrasonic Nozzle: Titanium Dioxide on Sapphire from Titanium (IV) Isopropoxide," *J. Amer. Cer. Soc.* 78:2763–2768 (1995).

*Primary Examiner*—Porfirio Nazario-Gonzalez
(74) *Attorney, Agent, or Firm*—Mueting, Raasch & Gebhardt, P.A.

(57) ABSTRACT

A method of forming a film on a substrate using Group III metal complexes. The complexes and methods are particularly suitable for the preparation of semiconductor structures using chemical vapor deposition techniques and systems.

13 Claims, 2 Drawing Sheets

METHODS, COMPLEXES, AND SYSTEM FOR FORMING METAL-CONTAINING FILMS

This is a division of application Ser. No. 08/725,064, filed Oct. 2, 1996, now U.S. Pat. No. 5,924,012, which is incorporated herein by reference.

FIELD OF THE INVENTION

This invention relates to methods and complexes for forming metal-containing films, such as metal or metal alloy films, particularly during the manufacture of semiconductor structures. The complexes include a Group III metal, and are particularly suitable for use in a chemical vapor deposition system.

BACKGROUND OF THE INVENTION

Aluminum is one of the three primary materials used today in semiconductor structures, the other two being silicon and silicon dioxide. It is primarily used in thin films as an interconnect between the specific structures formed on semiconductor substrates or substrate assemblies. Aluminum has been an important material in the fabrication of semiconductor structures because of its high conductivity, low resistivity (2.7 $\mu\Omega$-cm), high adherence to silicon and silicon dioxide, and low stress. And its use is expanding into other metallization applications. For example, it is being examined to replace tungsten in contacts or vias (i.e., very small openings located, for example, between surface conductive paths and or "wiring" and active devices on underlying layers), which are getting narrower and deeper, and harder to fill with metal.

Aluminum alloys are also used in semiconductor structures, including alloys of aluminum with copper, titanium, etc., and combinations thereof. The addition of small quantities (typically, about 0.1–4%) of other metals to aluminum improves the electromigration resistance and reduces the propensity of aluminum thin-films to form hillocks (i.e., protrusions on the aluminum film surface). Such films, however, have increased resistivity over that of pure aluminum films.

In some applications, aluminum films are deposited using sputtering techniques; however, sputtered aluminum is not effective at filling contacts or vias because of shoulders or overhangs that form at the contact openings. These overhangs can lead to the formation of keyhole-shaped voids. Various collimation techniques help reduce this problem, but typically not enough to enable complete filling of very small geometries (e.g., less than about 0.5 $\mu$m). Therefore, it is desirable to use chemical vapor deposition (CVD) to form aluminum and aluminum alloy films.

Dimethylaluminum hydride has emerged as one of the preferred materials for aluminum metallization by CVD. A serious problem with this material, however, is its pyrophoricity. This problem has been addressed to some degree by the addition of amines to the compound to act as stabilizing Lewis base donors to the aluminum center. However, such precursor compounds are still pyrophoric, albeit to a lesser extent, and an additional complicating factor is introduced into the vapor pressure behavior of the precursor as a result of dissociation of the amine. Thus, there is a continuing need for methods and precursors for the deposition of aluminum and aluminum alloy films, as well as other Group III metal or metal alloy films, on semiconductor structures, particularly using vapor deposition processes.

SUMMARY OF THE INVENTION

The present invention provides complexes and methods for forming metal-containing films, particularly Group III metal-containing films on substrates, such as semiconductor substrates or substrate assemblies during the manufacture of semiconductor structures. The method involves forming a metal-containing film using a Group III metal complex, preferably a Group III metal hydride complex. The metal-containing film can be used in various metallization layers, particularly in multilevel interconnects, in an integrated circuit structure.

The metal-containing film can be a single Group III metal, or a metal alloy containing a mixture of Group III metals or a Group III metal and one or more metals or metalloids from other groups in the Periodic Chart, such as copper, silicon, titanium, vanadium, niobium, molybdenum, tungsten, scandium, etc. Furthermore, for certain preferred embodiments, the metal-containing film can be a nitride, phosphide, arsenide, stibnide, or combination thereof. That is, the metal-containing film can be a Group III-V (e.g., GaAs) semiconductor layer.

Thus, in the context of the present invention, the term "Group III metal-containing film" or simply "metal-containing film" includes, for example, relatively pure films of aluminum, gallium, or indium, alloys of aluminum, gallium, and/or indium with or without other non-pnicogen metals or metalloids, as well as complexes of these metals and alloys with Group V elements (N, P, As, Sb) or mixtures thereof. The terms "single Group III metal film" or "Group III metal film" refer to films of aluminum, gallium, or indium, for example. The terms "Group III metal alloy film" or "metal alloy film" refers to films of aluminum, gallium, and/or indium alloys with or without other metals or metalloids, for example. That is, if there are no metals or metalloids from groups in the Periodic Chart other than Group III, the alloy films contain combinations of aluminum, gallium, and indium.

Preferably, the metal alloy films do not contain Group V metals or metalloids (i.e., pnicogens).

One preferred method of the present invention involves forming a film on a substrate, such as a semiconductor substrate or substrate assembly during the manufacture of a semiconductor structure, by: providing a substrate (preferably, a semiconductor substrate or substrate assembly); providing a precursor comprising one or more complexes of the formula:

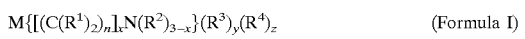

$$M\{[(C(R^1)_2)_n]_xN(R^2)_{3-x}\}(R^3)_y(R^4)_z \qquad \text{(Formula I)}$$

wherein: M is a Group III metal; each $R^1$, $R^2$, $R^3$, and $R^4$ is independently H or an organic group; x=1 to 3; n=1 to 6; y=1 when x=1 and y=3−x when x=2 or 3; and z=3−x−y; and forming a metal-containing film from said precursor on a surface of the substrate (preferably, the semiconductor substrate or substrate assembly). The metal-containing film is a Group III metal film or a Group III metal alloy film. Using such methods the complexes of Formula I are converted in some manner (e.g., decomposed thermally) and deposited on a surface to form a Group III metal-containing film. Thus, the film is not simply a film of the complex of Formula I.

The complexes of Formula I are neutral complexes and may be liquids or solids at room temperature. If they are solids, they are preferably sufficiently soluble in an organic solvent to allow for vaporization by flash vaporization, bubbling, microdroplet formation, etc. However, these complexes can also be vaporized or sublimed from the solid state using known chemical vapor deposition techniques.

Another method of the present invention involves forming a film on a substrate, such as a semiconductor substrate or substrate assembly during the manufacture of a semiconductor structure, by: providing a substrate (preferably, a semiconductor substrate or substrate assembly); providing a precursor comprising one or more hydride complexes of the formula:

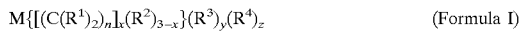

$$M\{[(C(R^1)_2)_n]_x(R^2)_{3-x}\}(R^3)_y(R^4)_z \quad \text{(Formula I)}$$

wherein: M is a Group III metal; each $R^1$, $R^2$, $R^3$, and $R^4$ is independently H or an organic group with the proviso that at least one of $R^3$ and $R^4$ is H; x=1 to 3; n=1 to 6; y=1 when x=1 and y=3−x when x=2 or 3; and z=3−x−y; and forming a metal-containing film from said precursor on a surface of the substrate.

Yet another method of forming a metal-containing film on a substrate, such as a semiconductor substrate or substrate assembly during the manufacture of a semiconductor structure, by: providing a substrate (preferably, a semiconductor substrate or substrate assembly); providing a liquid precursor comprising one or more hydride complexes of the formula:

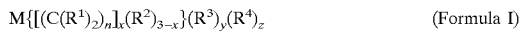

$$M\{[(C(R^1)_2)_n]_x(R^2)_{3-x}\}(R^3)_y(R^4)_z \quad \text{(Formula I)}$$

wherein: M is a Group III metal; each $R^1$, $R^2$, $R^3$, and $R^4$ group is independently H or a $(C_1-C_{30})$organic group, with the proviso that at least one of $R^3$ and $R^4$ is H; x=1 to 3; n=1 to 6; y=1 when x=1 and y=3−x when x=2 or 3; and z=3−x−y; vaporizing said liquid precursor to form vaporized precursor; and directing the vaporized precursor toward the substrate to form a metal-containing film on a surface of the substrate.

Thus, preferred embodiments of the methods of the present invention involve the use of one or more chemical vapor deposition techniques, although this is not necessarily required. That is, for certain embodiments, sputtering, spin-on coating, etc., can be used.

The methods of the present invention are particularly well suited for forming films on a surface of a semiconductor substrate or substrate assembly, such as a silicon wafer, with or without layers or structures formed thereon, used in forming integrated circuits. It is to be understood that the method of the present invention is not limited to deposition on silicon wafers; rather, other types of wafers (e.g., gallium arsenide wafer, etc.) can be used as well. Also, the methods of the present invention can be used in silicon-on-insulator technology. Furthermore, substrates other than semiconductor substrates or substrate assemblies can be used in the method of the present invention. These include, for example, fibers, wires, etc. If the substrate is a semiconductor substrate or substrate assembly, the films can be formed directly on the lowest semiconductor surface of the substrate, or they can be formed on any of a variety of the layers (i.e., surfaces) as in a patterned wafer, for example. Thus, the term "semiconductor substrate" refers to the base semiconductor layer, e.g., the lowest layer of silicon material in a wafer or a silicon layer deposited on another material such as silicon on sapphire. The term "semiconductor substrate assembly" refers to the semiconductor substrate having one or more layers or structures formed thereon. The compounds of Formula I incorporate features that make them selective for silicon over silicon dioxide.

Also, the present invention provides a hydride complex of Formula I wherein: M is a Group III metal (preferably Al, Ga, In); each $R^1$, $R^2$, $R^3$, and $R^4$ group is independently H or an organic group, with the proviso that at least one of $R^3$ and $R^4$ is H; x=1 to 3; n=1 to 6; y=1 when x=1 and y=3−x when x=2 or 3; and z=3−x−y.

A chemical vapor deposition system is also provided. The system includes a deposition chamber having a substrate positioned therein; a vessel containing a precursor comprising one or more complexes of Formula I wherein M is a Group III metal, each $R^1$, $R^2$, $R^3$, and $R^4$ group is independently H or an organic group, x=1 to 3, n=1 to 6, y=1 when x=1 and y=3−x when x=2 or 3, and z=3−x−y; and a source of an inert carrier gas for transferring the precursor to the chemical vapor deposition chamber.

DETAILED DESCRIPTION

Figure 1:
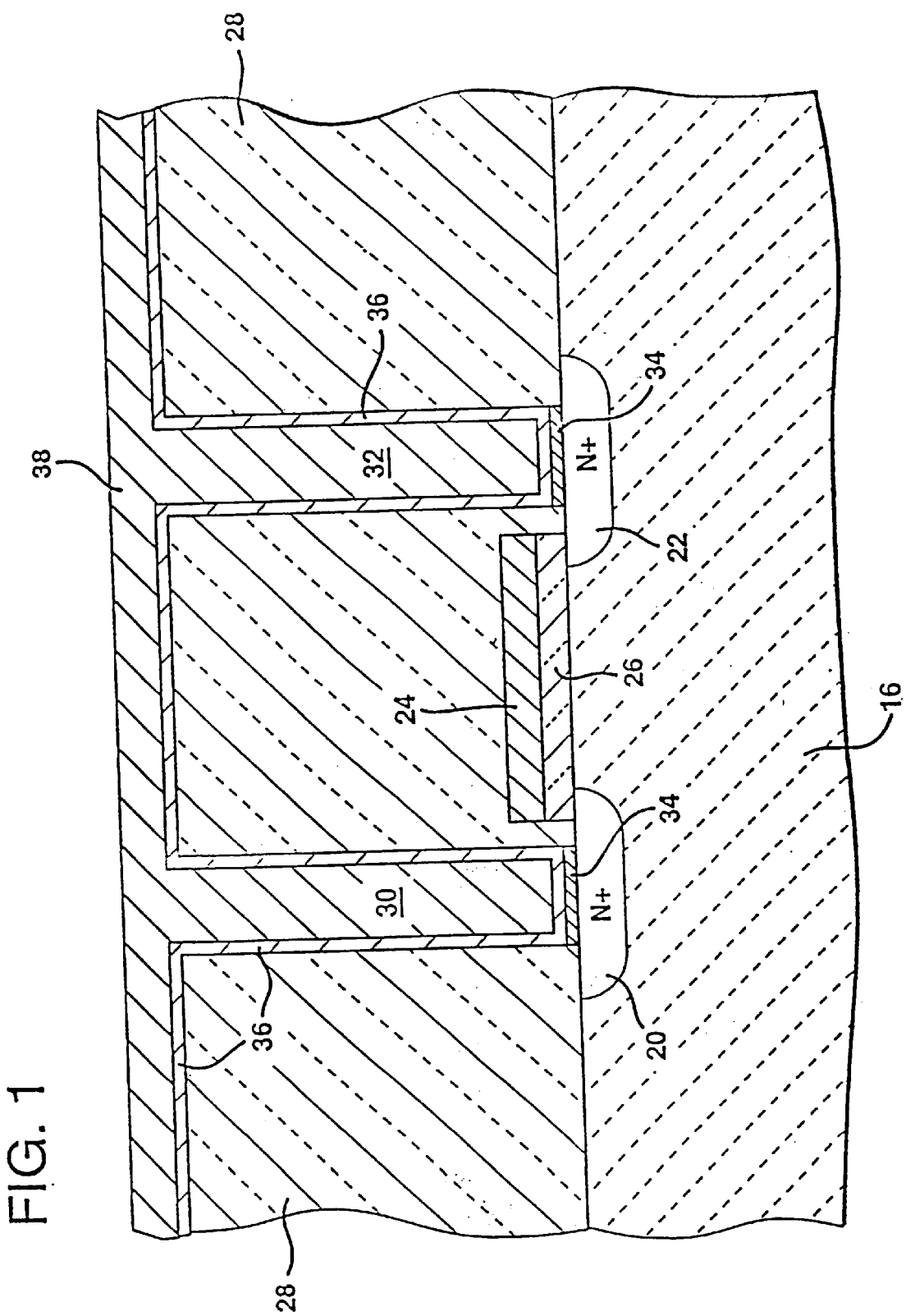
FIG. 1 is a cross-sectional schematic of a semiconductor contact or via having an aluminum film deposited in accordance with the method of the present invention.

The present invention provides a method of forming a Group III metal-containing film using one or more Group III metal complexes, preferably a Group III metal hydride complex. These complexes are mononuclear (i.e., monomers in that they contain one metal per molecule). Preferred embodiments display few intermolecular forces of attraction. Such complexes are generally volatile and transportable in the gas phase. They preferably have vapor pressures sufficiently low such that they are liquids at room temperature, although they can be solids. If they are solids, they are preferably soluble in organic solvents, such as aromatic and aliphatic hydrocarbons, nitriles, ethers, amines, etc., which allows for vaporization as a homogeneous mixture by direct liquid injection. They are also generally compatible with each other, so that mixtures of variable quantities of the complexes will not interact to significantly change their physical properties. Preferred embodiments are also generally nonpyrophoric.

Thus, many of the complexes described herein are suitable for use in chemical vapor deposition (CVD) techniques, such as flash vaporization techniques, bubbler techniques, and the microdroplet techniques. However, these complexes can also be vaporized or sublimed from the solid state using other known CVD techniques. Preferred embodiments of the complexes described herein are particularly suitable for low temperature CVD, i.e., deposition techniques involving temperatures of about 50–200° C.

One preferred method of the present invention involves vaporizing a precursor that includes one or more Group III metal complexes. For certain embodiments, the precursor can also include one or more Group V complexes (i.e., a compound containing N, P, As, or Sb). Also, the precursor can include complexes containing other metals or metalloids (preferably, non-pnicogen metals or metalloids).

The precursor can be vaporized in the presence of an inert carrier gas to form a relatively pure metal or metal alloy film. The inert carrier gas is typically selected from the group consisting of nitrogen, helium, and argon. In the context of the present invention, an inert carrier gas is one that does not interfere with the formation of the metal-containing film. Whether done in the presence of a carrier gas or not, the vaporization is preferably done in the absence of oxygen to avoid oxygen contamination of the films.

Alternatively, however, the precursor can be vaporized in the presence of a reaction gas to form a film. The reaction gas can be selected from a wide variety of gases reactive with the complexes described herein, at least at a surface under the conditions of chemical vapor deposition.

Examples of reaction gases include oxygen, nitrous oxide, ammonia, silane, water vapor, hydrogen sulfide, hydrogen selenide, hydrogen telluride. Various combinations of carrier gases and/or reaction gases can be used in the methods of the present invention to form metal containing films.

The Group III metal complexes described herein are four coordinate complexes having one multidentate ligand, which typically has at least one carbon atom that covalently bonds to the metal and one nitrogen atom that forms a dative bond with the metal. The designation "hydride complex" refers to a Group III metal complex containing at least one negatively charged hydride ligand in addition to the multidentate ligand. The multidentate ligand stabilizes the metal complex by incorporating the nitrogen donor atom into the ligand in such a way as to negate dissociation of the ligand prior to thermal decomposition.

The Group III metal complex is of the following formula:

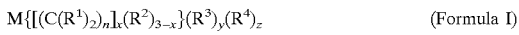

$$M\{[(C(R^1)_2)_n]_x(R^2)_{3-x}\}(R^3)_y(R^4)_z \quad \text{(Formula I)}$$

wherein: M is a Group III metal (preferably, Al, Ga, In); each R (i.e., $R^1$, $R^2$, $R^3$, $R^4$) is independently H or an organic group (preferably, with the proviso that at least one of $R^3$ and $R^4$ is H); x=1 to 3; n=1 to 6; y=1 when x=1 and y=3−x when x=2 or 3; and z=3−x−y. More preferably, $R^2$ is an organic group and at least one of $R^3$ and $R^4$ is H. The ligand $[(C(R^1)_2)_n]_xN(R^2)_{3-x}$ can bond to the central metal through the nitrogen and at least one of the $C(R^1)_2$ units. The $R^3$ and $R^4$ groups can be joined to form a ring or rings with the metal.

A preferred class of complexes of Formula I include hydride complexes wherein: M is a Group III metal (preferably, Al, Ga, In); each R (i.e., $R^1$, $R^2$, $R^3$, $R^4$) is independently H or an organic group, with the proviso that at least one of $R^3$ and $R^4$ is H; x=1 to 3; n=1 to 6; y=1 when x=1 and y=3−x when x=2 or 3; and z=3−x−y. For these hydride complexes, more preferably, $R^2$ is an organic group. This class of complexes of Formula I (i.e., the hydrides) are particularly advantageous because additional reducing equivalents are present in the complex (as a result of the hydride ligand(s)), which leads to less carbon contamination of the films formed upon decomposition of the complexes.

As used herein, the term "organic group" means a hydrocarbon group that is classified as an aliphatic group, cyclic group, or combination of aliphatic and cyclic groups (e.g., alkaryl and aralkyl groups). In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

In metal complexes such as this, substitution is not only tolerated, but is often advisable. Thus, substitution is anticipated in the complexes of the present invention. As a means of simplifying the discussion and the recitation of certain terminology used throughout this application, the terms "group" and "moiety" are used to differentiate between chemical species that allow for substitution or that may be substituted and those that do not so allow or may not be so substituted. Thus, when the term "group" is used to describe a chemical substituent, the described chemical material includes the unsubstituted group and that group with non-peroxidic O, N, or S atoms, for example, in the chain as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like.

For the R groups ($R^1$, $R^2$, $R^3$, and $R^4$) in the complexes of Formula I, H or ($C_1$–$C_{30}$)organic groups are preferred, H or ($C_1$–$C_{20}$)organic groups are more preferred, and H or ($C_1$–$C_8$)organic groups are most preferred. Of the organic groups, nonaromatic groups (e.g., aliphatic groups and alicyclic groups, which may or may not include unsaturation, and which may or may not include heteroatoms such as N, O, S, P, Si, etc.) are preferred. Of these, the aliphatic groups are more preferred, and alkyl moieties (particularly "lower" ($C_1$–$C_4$)alkyl moieties) are most preferred. The $R^3$ and $R^4$ groups can be joined to form a ring or rings.

Thus, the complexes of Formula I (wherein $R^1$=H, n=3, x=1, 2, or 3, $R^2$ is a lower alkyl moiety, and $R^3$ and $R^4$ are H or a lower alkyl moiety) can take the following forms (which are representative only):

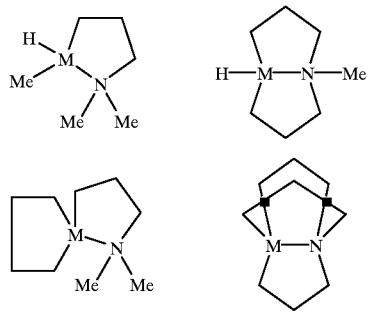

The complexes of Formula I are neutral complexes and may be liquids or solids at room temperature. If they are solids, they are preferably sufficiently soluble in an organic solvent to allow for vaporization by flash vaporization, bubbling, microdroplet formation, etc. However, these complexes can also be vaporized or sublimed from the solid state using known chemical vapor deposition techniques.

Various combinations of the complexes described herein can be used in precursors for chemical vapor deposition. Alternatively, certain complexes described herein can be used in other deposition techniques, such as sputtering, spin-on coating, and the like. Typically, those complexes containing R groups with a low number of carbon atoms (e.g., 1–4 carbon atoms per R group) are suitable for use with vapor deposition techniques. Those complexes containing R groups with a higher number of carbon atoms (e.g., 5–12 carbon atoms per R group) are generally suitable for spin-on or dip coating. Preferably, however, chemical vapor deposition techniques are desired because they are more suitable for deposition on semiconductor substrates or substrate assemblies, particularly in contact openings which are extremely small and require conformally filled layers of metal.

For preparation of films containing Group Ill-V (e.g., GaAs) semiconductor materials, the precursors described herein contain one or more complexes of Formula I and an appropriate source of the Group V element. Such sources of Group V elements include compounds such as $NH_3$, $PH_3$, $AsH_3$, $Me_3As$, $Me_3Sb$, $Me_3P$, $EtAsH_2$, $Me_2{}^tBuSb$, etc.

For the preparation of alloy films, two or more complexes of Formula I can be combined in a precursor mixture (e.g., $AlH_2(CH_2CH_2CH_2NMe_2)$ and $GaH_2(CH_2CH_2CH_2NMe_2)$ for an Al—Ga alloy). Alternatively, at least one complex of Formula I can be combined with another complex can be combined in a precursor mixture (e.g., $AlH_2(CH_2CH_2CH_2NMe_2)$ and $(Cu(PMe_3)(hfac)$ for an Al-Cu alloy).

The complexes of the present invention can be prepared by a variety of methods known to one of skill in the art. For example, $AlH_2(CH_2CH_2CH_2NMe_2)$ can be prepared by reacting $AlCl_3$ with $ClMg(CH_2)_3NMe_2$ followed by reduction.

As stated above, the use of the complexes of Formula I and methods of forming metal-containing films of the present invention are beneficial for a wide variety of thin film applications in semiconductor structures, particularly various metallization layers. For example, such applications include multilevel interconnects in an integrated circuit structure. Typically, thin films of Group III metals, such as aluminum, and alloys thereof are deposited as polycrystalline materials, usually in the 0.5–1.5 µm thickness range.

A specific example of where a film formed from the complexes of the present invention would be useful is the structure shown in FIG. 1. The substrate 16 may be in the form of an n-channel MOSFET (n-channel metal-oxide semiconductor field-effect transistor), which may be used in a DRAM memory device. As shown, substrate 16 is a p-type silicon having two n-type silicon islands 20 and 22, representing the transistor source and drain. Such a construction is well known. The gate for the transistor is formed by a metal/polysilicon layer 24 deposited over a silicon dioxide layer 26. A relatively thick layer of an insulating silicon dioxide 28 overlies the active areas on substrate 16.

To connect the MOSFET with conductive paths on the surface of the device, contacts 30 and 32 have been etched through oxide layer 28 down to the surface of substrate 16. A metal or metal silicide layer 34, such as titanium silicide, is deposited and formed at the base of contacts 30 and 32. A thin, conformal barrier layer of a refractory metal nitride 36 (e.g., titanium nitride, titanium aluminum nitride, titanium nitride silicide) is deposited over the walls of the contacts. Because of the presence of the conductive barrier layer, the electrical contact path is excellent and the aluminum metal 38 which is deposited over the refractory metal nitride barrier layer is prevented from attacking the substrate surfaces.

The method of the present invention can be used to deposit a metal-containing film, preferably a metal or metal alloy film, on a variety of substrates, such as a semiconductor wafer (e.g., silicon wafer, gallium arsenide wafer, etc.), glass plate, etc., and on a variety of surfaces of the substrates, whether it be directly on the substrate itself or on a layer of material deposited on the substrate as in a semiconductor substrate assembly. The film is deposited upon thermal decomposition of a Group III metal complex that is preferably either liquid at the temperature of deposition or soluble in a suitable solvent that is not detrimental to the substrate, other layers thereon, etc. Preferably, however, solvents are not used; rather, the Group III metal complexes are liquid and used neat. The method of the present invention preferably utilizes vapor deposition techniques, such as flash vaporization, bubbling, etc.

Conventional bubbler technology can be used to form films from the complexes of Formula I described above. In conventional bubbler technology, a carrier gas, typically nitrogen, is bubbled through the precursor (which is either a liquid or is dissolved in a liquid solvent) to sweep some of the precursor molecules into the processing chamber.

Alternatives to conventional bubbler technology include an approach wherein the precursor is heated and vapors are drawn off and controlled by a vapor mass flow controller. Further, another way is to pump the gas through the precursor using either a very precise metering pump or a liquid mass flow controller up to the point where it enters the reaction chamber. At that point, it can either be flash vaporized or injected directly into a mixing chamber and showerhead where it is vaporized. As described in the article entitled, "Metalorganic Chemical Vapor Deposition By Pulsed Liquid Injection Using An Ultrasonic Nozzle: Titanium Dioxide on Sapphire from Titanium (IV) Isopropoxide," by Versteeg, et al., *Journal of the American Ceramic Society*, 78, 2763–2768 (1995) a metalorganic CVD process utilizes pulsed on/off liquid injection in conjunction with atomization by an ultrasonic, piezoelectrically driven nozzle to deliver such metalorganic precursors. The pulse injection is said to allow control of film deposition rates, as fine as monolayers per pulse. The ultrasonic nozzle provides a mist of droplets into the processing chamber of a reactor for reproducible vaporization of the liquid precursor. Such a delivery system performs the vaporization in the processing chamber.

The complexes of Formula I are particularly well suited for use with vapor deposition systems, as described in copending application U.S. Ser. No. 08/720,710 entitled "Method and Apparatus for Vaporizing Liquid Precursors and System for Using Same," filed on even date herewith. Generally, using the method described therein, the vaporization of a liquid precursor or precursor dissolved in a liquid medium is carried out in two stages. First, the precursor is atomized or nebulized generating high surface area microdroplets or mist. In the second stage, the constituents of the microdroplets or mist are vaporized by intimate mixture of the heated carrier gas. This two stage vaporization approach provides a reproducible delivery for precursors (either liquid or dissolved in a liquid medium) and provides reasonable growth rates, particularly in device applications with small dimensions.

Figure 2:
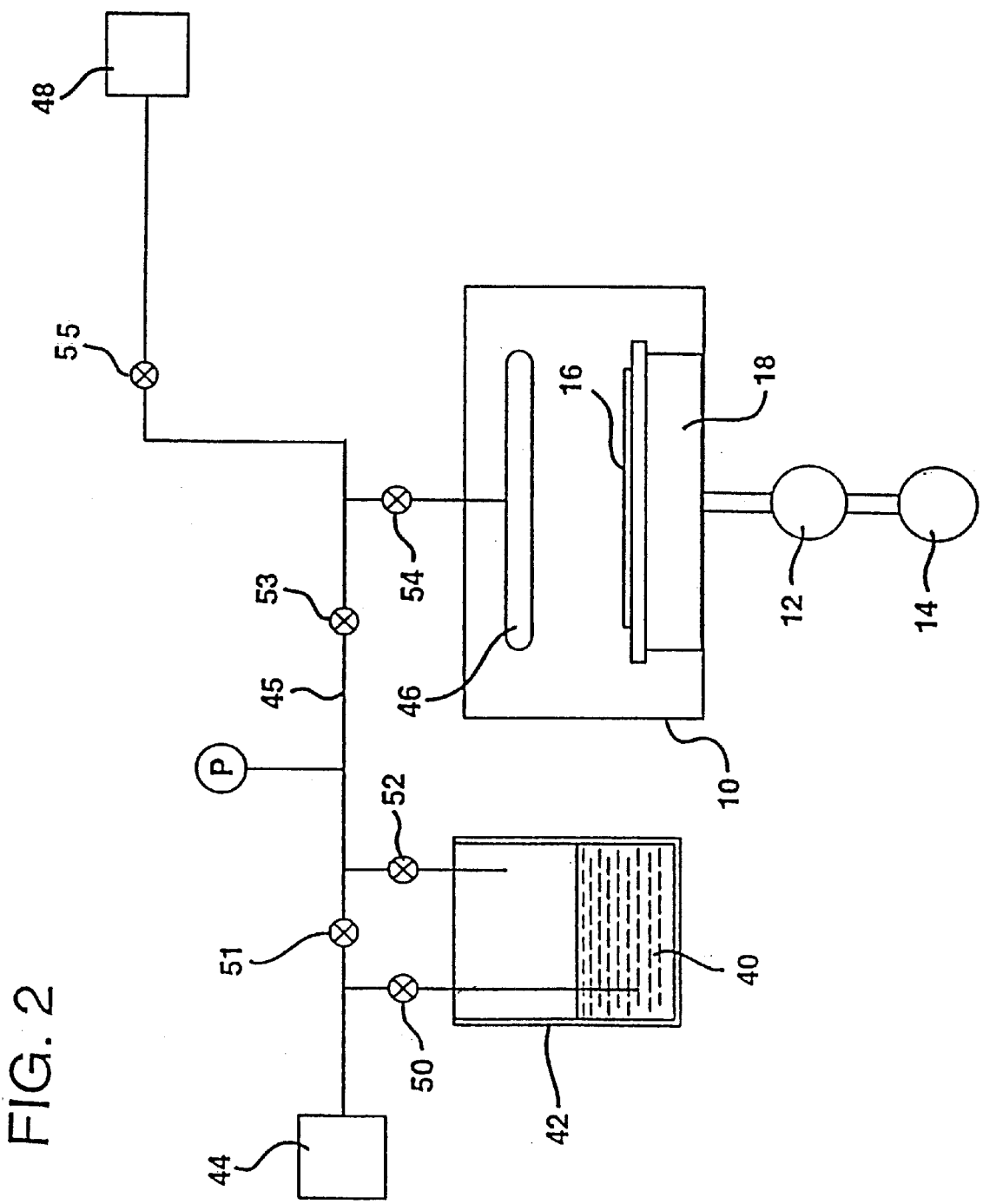
FIG. 2 is a schematic of a chemical vapor deposition system suitable for use in the method of the present invention.

A typical chemical vapor deposition (CVD) system that can be used to perform the process of the present invention is shown in FIG. 2. The system includes an enclosed chemical vapor deposition chamber 10, which may be a cold wall-type CVD reactor. As is conventional, the CVD process may be carried out at pressures of from atmospheric pressure down to about $10^{-3}$ torr, and preferably from about 1.0–0.1 torr. A vacuum may be created in chamber 10 using turbo pump 12 and backing pump 14.

One or more substrates 16 (e.g., semiconductor substrates or substrate assemblies) are positioned in chamber 10. A constant nominal temperature is established for the substrate, preferably at a temperature of about 0–600° C., and more preferably at a temperature of about 50–300° C. Substrate 16 may be heated, for example, by an electrical resistance heater 18 on which substrate 16 is mounted. Other known methods of heating the substrate may also be utilized.

In this process, the precursor 40, which contains one or more complexes of Formula I, is stored in liquid form in vessel 42. A source 44 of a suitable inert gas is pumped into vessel 42 and bubbled through the liquid, picking up the precursor and carrying it into chamber 10 through line 45 and gas distributor 46. Additional inert carrier gas may be supplied from source 48 as needed to provide the desired concentration of precursor and regulate the uniformity of the deposition across the surface of substrate 16. As shown, a series of valves 50–55 are opened and closed as required.

Generally, the precursor is pumped into the CVD chamber 10 at a flow rate of about 1–1000 sccm. The semiconductor substrate is exposed to the precursor at a pressure of about 0.001–100 torr for a time of about 0.01–100 minutes. In chamber 10, the precursor will form an adsorbed layer on the surface of the refractory metal nitride 36. As the deposition rate is temperature dependent, increasing the temperature of the substrate will increase the rate of deposition. Typical deposition rates are about 1000–10,000 Å/minute. The carrier gas containing the precursor is terminated by closing valve 53.

Various combinations of carrier gases and/or reaction gases call be used in certain methods of the present invention. They can be introduced into the chemical vapor deposition chamber in a variety of manners, such as directly into the vaporization chamber, in combination with the precursor, in combination (or in place of) the carrier gas.

The following examples are offered to further illustrate the various specific and preferred embodiments and techniques. It should be understood, however, that many variations and modifications may be made while remaining within the scope of the present invention.

EXAMPLES

Example 1
Preparation of $AlH_2(CH_2CH_2CH_2NMe_2)$ $AlCl_3$ (2.0 g, 15 mmol) is added to a dry flask under an inert atmosphere (e.g., argon). To this is added 30 mL of hexanes, and the resulting slurry is cooled to –40° C. A solution of $ClMgCH_2CH_2CH_2NMe_2$ (30 mL of 0.5 M in tetrahydrofuran) is added to the $AlCl_3$ over 10 minutes. The resulting mixture is stirred for 18 hours. The solvent is then removed in vacuo, resulting in a white solid, which is dried in vacuo and then transferred into a sublimator. A white sublimate of $AlCl_2(CH_2CH_2CH_2NMe_2)$ is obtained at 100° C. and a pressure of 0.5 torr. This product (2.0 g, 10.9 mmol) is dissolved in 30 mL of tetraethyleneglycol dimethylether (i.e., tetraglyme) and added to a suspension of $LiAlH_4$ (0.82 g, 21.8 mmol) in 20 mL of tetraglyme. After stirring for several hours, the product $AlH_2(CH_2CH_2CH_2NMe_2)$ is removed from the solvent by vacuum transfer into a liquid nitrogen-cooled receiver. The resulting colorless product is used for deposition of Al-containing films.

Example 2
Preparation of $In(CH_3)_2(CH_2CH_2CH_2NMe_2)$

This compound is prepared as described in Hostalek et al., *Thin Solid Films*, 174, 1 (1989).

Example 3
Preparation of $GaH(CH_3)(CH_2CH_2CH_2NMe_2)$ $GaCl_3$ (2.0 g, 11.4 mmol) is added to a dry flask under an inert atmosphere (e.g., argon) and suspended in 25 niL of tetrahydrofuran. To this suspension is added 22.8 mL (11.4 mmol) of a 0.5 M solution of $ClMgCH_2CH_2CH_2NMe_2$ in tetrahydrofuran. The mixture is stirred for 18 hours. The resulting solution is cooled to –60° C. and then 3.8 mL (11.4 mmol) of a 3.0 M solution of MeMgBr in diethyl ether is slowly added. The mixture is allowed to warm to room temperature, and after 2 hours the solvent is removed in vacuo. The intermediate, $GaCl(CH_3)(CH_2CH_2CH_2NMe_2)$, is then taken up in 30 mL of tetraglyme and added dropwise to a suspension of $LiAlH_4$ (0.43 g, 11.4 mmol) in 20 mL of tetraglyme. After several hours, the product $GaH(CH_3)(CH_2CH_2CH_2NMe_2)$ is removed from the solvent by vacuum transfer into a liquid nitrogen-cooled receiver. The resulting colorless product is used for deposition of Ga-containing films.

Example 4
Preparation of Aluminum Thin Films

A patterned semiconductor wafer is loaded into a CVD chamber, an d the wafer heated to approximately 250° C. The precursor, $AlH_2(CH_2CH_2CH_2NMe_2)$, is loaded into a conventional stainless steel bubbler inside a glove box, and the bubbler transferred to the CVD system. A helium carrier gas flow of 50 sccm is established through the bubbler, and a chamber pressure of 0.25 torr is established. The deposition is carried out until a desired thickness of aluminum is obtained on the wafer.

The foregoing detailed description and examples have been given for clarity of understanding only. No unnecessary limitations are to be understood therefrom. The invention is not limited to the exact details shown and described, for variations obvious to one skilled in the art will be included within the invention defined by the claims. The complete disclosurer of all patents, patent documents, and publications listed herein are incorporated by reference, as if each were individually incorporated by reference.

What is claimed is:

1. A hydride complex of the formula:

wherein:
(a) M is a Group III metal;
(b) each $R^1$, $R^2$, $R^3$, and $R^4$ group is independently H or a $(C_1–C_{30})$hydrocarbon group, with the proviso that at least one of $R^3$ and $R^4$ is H and none of the R groups are joined together to form ring systems; and
(c) n=1 to 6.

2. The complex of claim 1 wherein M is selected from the group consisting of Al, Ga, and In.

3. The complex of claim 1 wherein each $R^1$, $R^2$, $R^3$, and $R^4$ group is independently H or a $(C_1–C_{20})$ hydrocarbon group.

4. The complex of claim 1 wherein each $R^1$, $R^2$, $R^3$, and $R^4$ group is independently H or a $(C_1–C_4)$alkyl moiety.

5. The complex of claim 1 wherein M is Al.

6. The complex of claim 1 wherein $R^1$, $R^3$, and $R^4$ are each H, and $R^2$ is methyl.

7. The complex of claim 5 wherein $R^1$ and $R^3$ are each H, and $R^2$ and $R^4$ are each methyl.

8. The complex of claim 1 wherein M is Ga.

9. The complex of claim 8 wherein $R^1$, $R^3$, and $R^4$ are each H, and $R^2$ is methyl.

10. The complex of claim 8 wherein $R^1$ and $R^3$ are each H, and $R^2$ and $R^4$ are each methyl.

11. The complex of claim 1 wherein M is In.

12. The complex of claim 11 wherein $R^1$, $R^3$, and $R^4$ are each H, and $R^2$ is methyl.

13. The complex of claim 11 wherein $R^1$ and $R^3$ are each H, and $R^2$ and $R^4$ are each methyl.

* * * * *

UNITED STATES PATENT AND TRADEMARK OFFICE
CERTIFICATE OF CORRECTION

PATENT NO. : 6,326,505 B1  Page 1 of 1
DATED : December 4, 2001
INVENTOR(S) : Brian A. Vaartstra It is certified that error appears in the above-identified patent and that said Letters Patent is hereby corrected as shown below:

<u>Title page,</u>
OTHER PUBLICATIONS, in the Schumann et al. reference, please delete "{o-[(Dimethylamino) methly] Phenyl}" and insert -- {o-[(Diethylamino) methyl] phenyl} -- therefor.

<u>Column 9,</u>
Line 59, please delete "25 niL" and insert -- 25 mL -- therefor.

<u>Column 10,</u>
Line 14, please delete "an d" and insert -- and -- therefor.
Line 49, please delete "1" and insert -- 5 -- therefor.

Signed and Sealed this

Third Day of September, 2002

*Attest:*

JAMES E. ROGAN
*Director of the United States Patent and Trademark Office*

*Attesting Officer*